(12) United States Patent
Hsiao et al.

(10) Patent No.: US 7,396,912 B2
(45) Date of Patent: Jul. 8, 2008

(54) COLLAGEN PRODUCTION METHOD

(75) Inventors: Chin Ying Hsiao, Taipei (TW); Chiang Hung Chou, Chiai (TW); Hsi Wen Sun, Banciao (TW); June Nam Seah, Singapore (SG)

(73) Assignee: EcoDynamic BioLab, Wunshan District, Taipei (TW)

( * ) Notice: Subject to any disclaimer, the term of this patent is extended or adjusted under 35 U.S.C. 154(b) by 62 days.

(21) Appl. No.: 10/822,938

(22) Filed: Apr. 12, 2004

(65) Prior Publication Data

US 2004/0253678 A1   Dec. 16, 2004

Related U.S. Application Data

(60) Provisional application No. 60/462,528, filed on Apr. 11, 2003.

(51) Int. Cl.
*A61K 38/39* (2006.01)
(52) U.S. Cl. .................................. 530/356; 530/412
(58) Field of Classification Search ................. 530/356, 530/412; 435/69.1
See application file for complete search history.

(56) References Cited

U.S. PATENT DOCUMENTS

| | | | |
|---|---|---|---|
| 3,616,205 A | 10/1971 | Ito et al. | |
| 3,681,093 A | 8/1972 | Tsuzuki et al. | |
| 4,064,008 A * | 12/1977 | Petersen et al. | 435/273 |
| 4,066,083 A * | 1/1978 | Ries | 435/273 |
| 5,106,949 A | 4/1992 | Kemp et al. | |
| 5,436,135 A | 7/1995 | Tayot et al. | |
| 5,480,427 A | 1/1996 | Kelman et al. | |
| 6,372,794 B1 | 4/2002 | Nimni | |

FOREIGN PATENT DOCUMENTS

| | | |
|---|---|---|
| DE | 25 07 223 A1 | 9/1976 |
| GB | 2 189 492 A * | 10/1987 |
| JP | 2004-173653 A | 6/2004 |

OTHER PUBLICATIONS

Rama et al. Distribution of different molecular species of collagen in the vertebral cartilage of shark (*Carcharius acutus*). Connective Tissue Res. 1984. 12, 2, 111-118.*
Orth et al. Non-reproducible collagen cross-linking in cartilage from broiler chickens with tibial dyschondroplasia. Avian Dis. 1994. 38, 1, 44-49.*
List of current species in the genus *Bacillus* from the German National Resource Center for Biological Materials; pp. 1-23.*
Schallmey et al. Developments in the use of *Bacillus* species for industrial production. Canadian Journal of Microbiology. 2004. vol. 50, No. 1, pp. 1-17.*
List of current species in the genus *Bacillus* from the German National Resource Center for Biological Materials; pp. 1-23, 2004.*
Asdornnithee, Somsit et al., "Isolation and Characterization of a Collagenolytic Enzyme from *Bacillus licheniformis* N22," *Journal of Fermentation and Bioengineering*, 78(4): 283-287, 1994.
Cristescu, Dumitru et al., "Depolymerization of skin collagen by bacterial enzymes," *Chemical Abstract 427217*, 1 page, 1974.
Makinen, Kauko K. et al., "Purification and Properties of an Extracellular Collagenolytic Protease Produced by the Human Oral Bacterium *Bacillus cereus*." *The Journal of Biological Chemistry*, 262(26): 12488-12495, 1987.
Nakayama, Toru, "Thermostable Collagenolytic Activity of a Novel Thermophilic Isolate, *Bacillus* sp. Strain NTAP-1," *Journal of Bioscience and Bioengineering*, 89(6), 612-614, 2000.
PCT International Search Report for PCT/IB2004/001439, mailing date Oct. 7, 2004, received Oct. 13, 2004.
Gross J. and Kirk D. (1958) J Biol Chem. 233(2):355-360.
Gross J. and Lapiere C. M. (1962) Proc Natl Acad Sci U S A. 48:1014-1022.
Gross J. and Nagai Y. (1965) Proc Natl Acad Sci U S A. 54(4):1197-1204.
Stricklin G. P. and Hibbs M. S. (1988) Collagen, vol. I Biochemistry, Chapter 8, Biochemistry and Physiology of Mammalian Collagenases: 187-205 and Table of Contents of vol. I-III.
Wallace D. G., McPherson J. M., Ellingsworth L., Cooperman L., Armstrong R., and Piez K. A. (1988) Collagen, vol. III Biotechnology, Chapter 5, Injectable Collagen for Tissue Augmentation: 118-144 and Table of Contents of vol. I-III.

* cited by examiner

*Primary Examiner*—Karen Cochrane Carlson
(74) *Attorney, Agent, or Firm*—Finnegan, Henderson, Farabow, Garrett, & Dunner LLP

(57) ABSTRACT

The present invention relates to a novel collagen production method wherein the collagen-containing tissues are fermented to extract the collagen. The fermentation process employs microorganisms, including but is not limited to bacteria and yeast. The present invention is also directed to collagen product comprising collagen produced by fermentation.

26 Claims, 6 Drawing Sheets

Electrophoresis of avian collagen on a 7.5% polyacrylamide gel. α and β denote different collagen configurations.

Separation of porcine collagen on a 10% polyacrylamide gel. α, β and γ denote different collagen configurations.
Lanes 1, 2 porcine collagen, 20 μg and 40 μg; lanes 3, 4 commercial bovine collagen, 40 μg and 20 μg

8% SDS-PAGE

Lane 1:
 10 μl
Lane 2:
 20 μl

8% SDS-PAGE

Lane 1: 5 μl
Lane 2: 10 μl
Lane 3: 20 μl
Lane 4: 40 μl

8% PAGE-SDS

Lane 1 : marker
Lane 2 : 5 μl
Lane 3 : 10 μl

COLLAGEN PRODUCTION METHOD

DESCRIPTION OF THE INVENTION

This application claims the benefit of U.S. Provisional Application No. 60/462,528, filed Apr. 11, 2003, which is incorporated herein by reference.

FIELD OF THE INVENTION

This invention relates generally to a novel collagen production method and more particularly to the extraction of collagen from collagen-containing tissues using a fermentation process and to the collagen product produced thereby.

BACKGROUND OF THE INVENTION

Collagen is the principal protein component of the extracellular matrix. In mammals, collagen sometimes constitutes as much as 60% of the total body protein. It comprises most of the organic matter of skin, tendons, bones and teeth, and occurs as fibrous inclusions in most other body structures. Collagen is also the principal ingredient in fish skins.

There are many types of collagen which differ from each other to meet the requirements of various tissues. Currently, animal collagen types I through XIX have been discovered, and of these, collagen types I through V are used in a variety of ways as medical and cosmetic materials as well as food supplements. In particular, type I collagen is used most commonly as an extra cellular matrix. These collagens are extracted and purified from the connective tissue of various organs such as skin, bone, cartilage, tendon, and viscus of animals such as cows, pigs, birds, kangaroos and so forth by acidic solubilization, alkaline solubilization, neutral solubilization and or enzymatic solubilization.

In alkaline solubilization, salt solutions are used to extract the salt-soluble fractions of collagen which is a small fraction with minimal crosslinking.

Dilute acid solutions are also been used to extract collagen from young rapidly growing tissues. The acid-soluble fraction is slightly greater than the salt soluble fraction. However, at times, the extraction solutions may be more dangerous to handle due to their acidic pH (Gross et al., Proc. Natl. Acad. Sci U.S.A., 41, pp 1-7 (1955) and Davison et al, Conn. Tiss. Res., 1, pp 205-216 (1972)).

Enzymatic solubilization, e.g., use of pepsin, is also employed to solubilize another fraction of collagen. Enzyme extraction is preferable in many instances because this methodology produces increased yields and higher purity collagen. However, enzyme extraction suffers the disadvantage of producing partially degraded collagen, i.e., the extraction enzyme cleave the collagen molecule at the terminal non-helical regions which contain the inter-collagenous crosslinkages. It has been found that collagen extracted by use of the enzyme pepsin, a frequently used enzyme for the production of enzyme-extracted collagen, produces living tissue equivalents which are undesirably weak for certain applications, e.g., those which involve substantial mechanical handling of the tissue equivalent.

Thus, there is the need for improved collagen compositions and methods of preparing such compositions.

SUMMARY OF THE INVENTION

The present invention addresses this problem by providing a novel collagen production method wherein a fermentation process is employed to obtain collagen from collagen-containing tissues. Fermentation is the microorganisms' aerobic or anaerobic biological oxidation of organic compounds, such as glucose, to yield ATP and simpler organic compounds which are needed by the cell for biosynthetic or assimilatory reactions (Samuel, B. et al., Medical Microbiology $4^{th}$ Ed. Section 1 (1996)). Microorganisms are capable of generating a wide array of molecules as end points to fermentation. Collagen-containing tissues can be subjected to fermentation by different microorganisms, including but not limited to those that are considered as Generally Regarded As Safe (GRAS). Collagen-containing tissues that have been subjected to fermentation reactions can result in better quality collagen and greater collagen extraction yields. The application of fermentation also reduces the use of chemical and organic solvents that may be harmful to the environment and the workers.

Therefore, collagen extraction via fermentation has many advantages. Collagens extracted via fermentation have an increased purity, comprising mostly of well-preserved collagen monomers, whereas collagens extracted by methods in the prior art have more collagen polymers and small molecular weight protein impurities. Also, the collagen yield is about 5 to 10 times of that produced by methods in the prior art. Furthermore, the use of fermentation reduces the use of chemical and organic solvents used in the extraction process. In fact, unlike methods in the prior art where a large amount of alkali solvents are used, in the present invention, no alkali solvents are used to treat the collagen-containing tissues. Thus, the present invention is also a better option for the reason of environmental protection.

All collagen types can be extracted via fermentation, and the separation of different collagen types has been well documented for their solubility in solution with different ionic strengths and pH. It is well established that collagen type I, II, and III can and have been separated, after extraction, based on their difference in ionic strength. Separation of type I and III collagen can be achieved by interrupted electrophoresis, which is well known to those skilled in the art (Skyes, B., et al, Biochemical and Biophysical Research Communications 72(4):1472-1480 (1976)). Type I collagens are primarily present in the dermis layer and in the tendon. Type II collagens are predominantly found in the cartilage. Type III collagens are also found in the dermis layer.

The present invention is directed to the method of utilizing fermentation to obtain collagen.

The invention relates to collagen obtained via fermentation involving microorganisms such as bacteria or yeast.

Alternatively, the invention provides for dissolving the fermented tissues in acidic solution after fermentation. In another embodiment, after solubilization in the acidic solution, collagens are precipitated out by the addition of salt.

The present invention is also directed to collagens produced by fermentation and collagen thus produced.

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
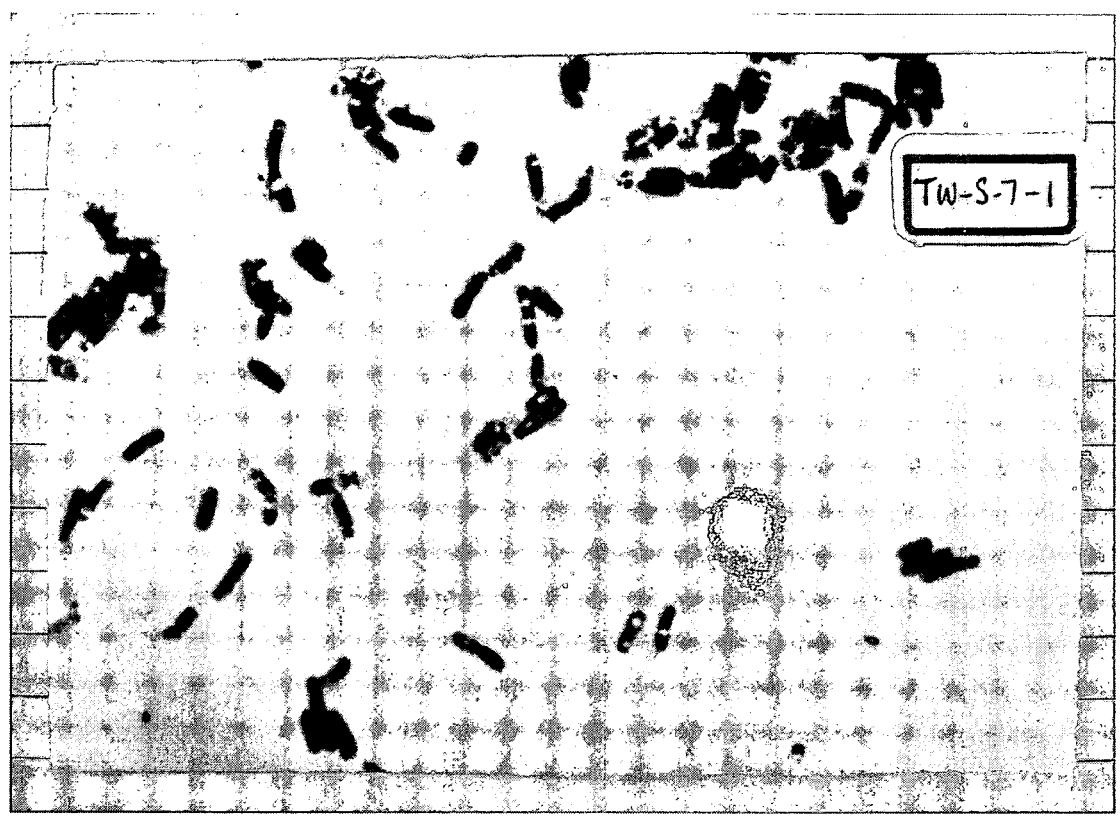
FIG. 1 is a photo of Gram staining of bacterial isolate TW-S-7-1.

The present invention is directed to a novel process for producing collagen, wherein collagens are obtained via fermentation involving microorganisms. In addition, the invention further provides for acidic solubilization of the fermented tissues and the subsequent precipitation of the extracted collagen by the addition of salt. The present invention also provides for collagen thus produced by the fermentation process and collagen products containing such collagen.

Definitions

As used herein, the term "collagen" refers to the main protein of connective tissue that has a high tensile strength and that has been found in most multicellular organisms. Collagen is a major fibrous protein, and it is also the non-fibrillar protein in basement membranes. It contains an abundance of glycine, proline, hydroxyproline, and hydroxylysine. Currently, collagen types I-XIX have been identified and they differ by the amino acid structure of the alpha chain. The term "collagen" as used herein is understood as meaning all collagen types and any form of collagen, whether native nor not, atelocollagen, insoluble collagen, collagen fibers, soluble collagen, and acid-soluble collagen.

As used herein, the term "collagen-containing tissues" refers to any tissue that contains collagen, including but not limited to tendon, skin, cornea, bone, cartilage, teeth, intervertebral disc, fetal skin, cardiovascular system, basement membrane, placenta, and anchoring fibrils beneath any epithelia.

As used herein, the term "collagen product" refers to any product which contains at least one collagen, and any derived product, including hydrolyzates. The hydrolyzates can be obtained chemically or enzymatically in a manner well known to those skilled in the art. The collagen or derivatives thereof can be in totally minor or major proportions, irrespective of its form.

As used herein, the term "hydrolyzing" refers to being subject to hydrolysis, a chemical reaction in which water is used to break down a compound; this is achieved by breaking a covalent bond in the compound by inserting a water molecule across the bond.

As used herein, the terms "fermenting" and "fermentation" refer to the aerobic or anaerobic process in which microorganisms such as bacteria, yeast, and other small organisms metabolizes one or more substances to produce the energy and chemicals it needs to live and re-produce. This process of chemical reactions will produce some form of by-product. Microorganisms are capable of generating a wide array of molecules as end points to fermentation. For example, carbon dioxide and ethanol are the by-products produced in brewing by yeast and pyruvate is converted into lactic acid in lactic acid fermentation. Fermentation is an ATP-generating process in which organic compounds act as both donors and acceptors of electrons, and it can take place in the absence of $O_2$ (Berg, M. Jeremy et al. Biochemistry chap. 16 (2002)).

As used herein, the term "microorganism" refers to a living organism too small to be seen with the naked eye, including bacteria, fungi, protozoans, algae, and viruses.

As used herein, the term "GRAS" refers to Generally Regarded as Safe Microorganisms that are known to one skilled in the art, including but not limited to *Bacillus, Lactobacillus, Pseudomonas* and yeast As used herein, the term "nutrient medium" refers to a medium containing the necessary substances for the growth and sustainment of the microorganisms' life.

As used herein, the term "avian" means of, relating to or derived from birds.

As used herein, the term "aquatic animals" refers to air-breathing and non-air-breathing animals that grow and live in water including but not limited to fish, jelly fish, crustaceans such as prawns and crabs, and cephalopods such as squids and octopuses.

As used herein, the term "porcine" means of, relating to or derived from pigs.

As used herein, the term "acidic solutions" refers to a solution with one or more of the following characteristics: a sour taste, turns blue litmus paper red, and contains compounds that can combine with metals to form salts. The solution has a pH value of lower than 7. Examples of acidic solutions include but are not limited to solutions of acetic acid, citric acid, formic acid, hydrochloric acid, sulfuric acid, nitric acid, phosphoric acid, propionic acid, and lactic acid or the like.

As used herein, the term "salt" refers to any of numerous compounds that result from replacement of part or all of the acid hydrogens of an acid by a metal or a group acting like a metal, including but not limited to sodium chloride, potassium chloride, calcium chloride, magnesium chloride, ammonia sulfate, sodium sulfate, potassium acetate, and sodium acetate or the like.

As used herein, the term "filtration" refers to a filtering process or any other process having the effect of filtering, e.g. centrifugation, distillation, dialysis or any other process having the effect of separating out matter in suspension.

Collagen Production Using Fermentation

The present invention is directed to a method of producing collagen comprising providing collagen-containing tissues, providing microorganisms, and allowing the microorganisms to ferment the collagen-containing tissues. Fermentation is the aerobic or anaerobic process in which microorganisms such as bacteria, yeast, and other small organisms metabolizes one or more substances to produce the energy and chemicals it needs to live and re-produce, and in which some form of by-product is produced. The collagen-containing tissues may be obtained from mammals, aquatic animals, or birds. Once collagen-containing tissues are being subjected to the fermentation process, collagen composition comprising mostly of collagen monomers can be readily extracted therefrom in much higher yield, as compared to yields from other methods in the prior art.

The fermentation of the collagen containing tissue is carried out by using microorganisms. In one specific embodiment, the microorganism comprises bacteria. In a more particular embodiment of the invention, the bacteria used are Gram positive. In a still more specific embodiment of the invention, bacteria belonging to the genus *Bacillus* are employed. Alternatively, the fermentation is carried out by using microorganisms comprising yeast. In another embodiment, the fermentation is carried out by using microorganisms comprising GRAS microorganisms. In a more specific embodiment, the fermentation is carried out by using microorganisms that are GRAS Gram positive microorganisms.

In another embodiment of the invention, the collagen-containing tissues are obtained from mammals, aquatic animals, or birds.

In another embodiment, the invention further comprises extracting the collagen by dissolving the fermented tissues in acidic solutions as defined above. In a more specific embodiment, extracting the collagen further comprises removing insoluble tissues from the acidic solutions by filtration. In a further embodiment, extracting the collagen further comprises precipitating the collagen from the acidic solution containing the fermented tissues by adding salt as defined above. In a more specific embodiment, the precipitated collagens are collected by filtration. Another embodiment further provides hydrolyzing the extracted collagen. Hydrolyzation can be carried out via various methods well known to one skilled in the art, such as acid treatment, alkali treatment, heat denaturation followed by protease cleavage, ultrasonic method, and collagenase treatment.

A more specific embodiment of the invention relates to a method of producing collagen comprising the following steps. First, collagen-containing tissues are provided from one or more of mammalian, avian or aquatic animal sources. Then Gram (+) bacteria belonging to the genus *Bacillus* are provided. Next, the collagen-containing tissues are fermented in a fermenter, at the amount of about 10% w/v, together with about 160 ul of the bacteria and nutrient medium. Subsequently, the fermented tissues are dissolved in aqueous solutions, which contains about 0.5M acetic acid, at pH about 3.0, and about 1% w/v pepsin. Then the insoluble tissues are removed by filtration or, as defined above, any other process having the same effect as filtration. Next, salt is added to the acetic acid solutions containing the fermented tissues and kept undisturbed overnight to precipitate the collagen.

Another embodiment of the invention directs to a method of producing collagen comprising the following steps. First, collagen-containing tissues from one or more of mammalian, avian, or aqutic animal sources are provided. Next, Gram (+) bacteria belonging to the genus *Bacillus* are provided. Then, the collagen-containing tissues are fermented in a fermenter at the amount of about 10% to about 40% w/v, together with about 10 ul of the bacteria and nutrient medium. Subsequently, the fermented tissues are dissolved in aqueous solutions which contains about 0.5M acetic acid, at pH about 3.0, and about 0.4% to 2% w/v pepsin.

Collagen and Collagen Product

The present invention is also directed to a collagen product comprising the collagen monomers obtained from collagen-containing tissues via fermentation. The collagen product can be any product which contains at least one collagen, and any derived product, including hydrolyzates. The hydrolyzates can be obtained chemically or enzymatically in a manner well known to those skilled in the art. The collagen or derivatives thereof can be in totally minor or major proportions, irrespective of its form. In a more particular embodiment, the fermentation is carried out by employing microorganisms comprising bacteria. In a more specific embodiment, the bacteria employed in the fermentation process is Gram positive. Alternatively, the bacteria employed is of the genus *Bacillus*. In another embodiment, the microorganisms used in the fermentation process comprises yeast. Then again, microorganism used in the fermentation process comprises GRAS microorganisms. In a more specific embodiment, the collagen-containing tissues are obtained from mammals, aquatic animals, or birds.

In another embodiment, the present invention is directed to a collagen product comprising collagen monomers. In one embodiment, the collagen product comprises about at least about 10% collagen monomers by weight with regard to the total collagen weight in the collagen product. In a more specific embodiment, the amount is at least about 50%, and in another particular embodiment, at least about 80%.

Collagen products can be used for many applications, such as medical material, pharmaceutical, cosmetic, and food applications etc.

Among the various materials used as medical materials, collagen is biologically suitable. Advantages of collagen include one or more of the following characteristics: excellent bioaffinity and histocompatibility; low antigenicity (collagen is a relatively weak immunogen, due in part to masking of potential antigenic determinants by its triple helix structure); high resistance to proteolysis due to its helical structure; ability to promote host cell differentiation and growth; hemostatic action; natural substance for cell adhesion and the major tensile load-bearing component of the mucsulo-skeletal system; ability to be completely broken down and absorbed in the body. Consequently, it has properties that are particularly suitable for use as a medical material. Because of these properties, collagen has application in the manufacture of implantable prostheses, in the preparation of living tissue equivalents, in making cell growth matrices, in making dressings for a burn or wound or a sheathing for repairing damaged tendons, etc.

In all applications, high quality collagens are much desired and sought after. It is appreciated that highly refined collagen with less impurities is adaptable not only for use as an element of food products, but also for various industrial uses, such as for medical materials, cosmetic materials and emulsifier for photographic films. Denaturation and degradation of collagen often occurs in methods in the prior art and limit the collagen's use in both food and industrial fields. However, collagen extraction via fermentation as described in the present invention can result in well-preserved collagen monomers, which can serve as a valuable collagen source for commercial and medical use.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

The following examples further illustrate the invention. They are merely illustrative of the invention and disclose various beneficial properties of certain embodiments of the invention. The following examples should not be construed as limiting the invention.

EXAMPLES

The practice of the present invention will employ, unless otherwise indicated, conventional techniques of cell biology, cell culture and fermentation which are within the skill of the art. Such techniques are explained fully in the literature.

Example 1

Identification of Bacterial Isolate Used in Collagen Extraction Fermentation

Preparation of Bacterial Culture

Bacteria were collected from fields and used in fermentation to extract collagen from collagen-containing tissues as described above. These bacteria were identified as bacterial isolate TW-S-7-1. In preparation of the bacterial culture for identification, the bacteria isolates was streaked out on a nutrient agar plate. The plate was then incubated at 37° C. for 16 hours. Then five single colonies of the bacteria were inoculated in five different "L" shape test tubes with each containing 5 ml of fresh nutrient broth. The test tubes were kept at 37° C. with agitation (50-200 rpm) for 16-24 hours. Another test tube was also prepared as a negative control with 5 ml of fresh nutrient broth without any bacteria inoculation. The control test tube was incubated at 37° C. with agitation (50-200 rpm).

Turbidity was observed in all five test tubes with bacterial inoculation, indicating proliferation of the microorganisms. No sign of growth was observed in the negative control test tube.

Gram Staining

Gram staining was carried out on the TW-S-7-1 bacteria. First, a drop of freshly cultured bacteria was applied onto a clean slide and spread evenly. The smear was fixed by heating over a flame for 10 seconds. Then the fixed smear on the slide was flooded with 1% crystal violet for 60 seconds. Excess dye was poured off and the slide was washed gently with tap water. A paper towel was applied to drain of the water on the slide. The specimen appeared blue-violet when observed with the naked eye.

Subsequently, the smear was washed with Gram's iodine for 60 seconds. Then more Gram's iodine was added and left on the smear for another 60 seconds. Then, the smear slide was washed with tap water and drained with paper towel.

Subsequently, the smear slide was washed with 95% ethanol for 30 seconds and then washed with tap water to stop decolonization. 0.25% safranin was applied to the slide for 30 seconds for counter staining. Then, the slide was washed with tap water, drained and blotted with paper towel, and examined under oil immersion field.

The cell's morphology, relative size, and staining pattern were documented, see FIG. 1. Numerous rod-shaped structures can be easily spotted. All rod-shaped structures have a dark blue coloration, thus they are Gram positive. The length of the structure was estimated to be around 1-1.5 µm. The refractive oval or ellipsoidal fine structure found inside the rod-shaped structure is bacterial endospore.

Catalase Assay

30 µl of fresh TW-S-7-1 bacterial culture was smeared onto the slide and air dried for 3 minutes. An aliquot of hydrogen peroxide ($H_2O_2$) solution (30% v/v) was carefully applied to cover the smear completely and then the smear was incubated at room temperature for 5 minutes. Formation of gas bubbles denotes the production of catalase by the bacteria.

When the $H_2O_2$ solution (3% v/v) was added, bubbling occurred immediately. Catalase is produced by the cell to remove $H_2O_2$ from the cell by turning it into water and oxygen.

Result

The tested bacterial isolate TW-S-7-1 retained the violet color of the Gram staining and is thus Gram positive. It is 1-1.5 µm in length. It also produces catalase in the catalase assay. Therefore, the isolate TW-S-7-1 is identified as belonging to the genus *Bacillus*.

Example 2

Production of Collagen from Avian Tissues Using Bacterial Fermentation

About 800 grams of chicken feet were washed thoroughly with tap water. Approximately 400 grams of soft tissue including flesh, skin and tendon (collectively known as tissues) were collected from these materials and cut into small pieces (0.5 cm in length and width). These tissues were soaked in 70% ethanol for 15 minutes before air-dried in a biosafety hood for 0.5-2 hours.

A field isolate Gram (+) bacterium, belonging to the genus *Bacillus*, was used in the fermentation process utilized to extract collagen from the tissues. A loop (approximately 10 µl) of fresh bacterial culture was individually inoculated. The microorganism was cultured in nutrient medium at 37° C. for 24 hours with constant shaking at 150 rpm. The bacterial culture was transferred into four 125 ml hinton flasks, with each containing 25 ml nutrient medium, and allowed to grow for 24 hours with constant shaking at 250 rpm. The content of each flask was proportionally scaled up to 100 ml and allowed to grow for another 24 hours. Prior to fermentation, bacterial culture from all four flasks were transferred to a 6-liter fermenter that contained 4 liters of nutrient medium and allowed to grow at 37° C. for 24 hours. For the bacterial growth condition, the agitation and aeration rate were set at 450 rpm and 3 vvm, respectively.

The fermenter was then loaded (10% w/v) with the avian tissues prepared as described above. The growth conditions remained unchanged except that the agitation was subsequently adjusted to 350 rpm. Fermentation proceeded for 24 hours. When fermentation was completed, fermented avian tissues were carefully separated from the culture broth and washed thoroughly with double distilled water.

Avian collagen, particularly type I collagen, was readily extracted by dissolving the fermented tissues in an aqueous solution (3% w/v)) containing 0.5M acetic acid (pH 3.0) and 1% pepsin (w/w) with gentle stirring at 4° C. for 48 hours.

The insoluble tissues that remained after dissolving the fermented tissues and large particles in the acidic solution collected were removed by a 30 μm tangential filtration at 4° C. Filtered solution was later subject to delipidation, which was accomplished by filtering the acidic solution through fine granule activated charcoals at 4° C. Insoluble materials including charcoal particles were removed by centrifuging the solution at 5000×g for 50 minutes.

560 grams of salt were added slowly to the resulting cold acidic solution from above with gentle stirring until it was fully dissolved. The solution was kept undisturbed at 4° C. overnight, allowing collagen to precipitate slowly. Precipitated collagen was concentrated by centrifuging the mixtures at 2000×g for 50 minutes at 4° C. Supernatant was carefully discarded and a collagen-containing pellet with milky color appearance was re-dissolved in a freshly prepared acid aqueous solution containing 0.5M acetic acid with gentle stirring at 4° C.

Crude avian type I collagen-containing solution was further purified by filtering through a 3 μm pore size filter membrane. The flow-through was refined by a reverse osmosis filtration using a 0.2 μm pore size spiral wound cartridge. To enrich avian type I collagen, the solution was concentrated by another reverse osmosis filtration using a 50 kilodalton cut-off spiral wound cartridge. This filtration step was repeated to enhance the enrichment and to maximize the removal of small peptides or other contaminants with molecular weight less than 50 kilodalton.

Figure 2:
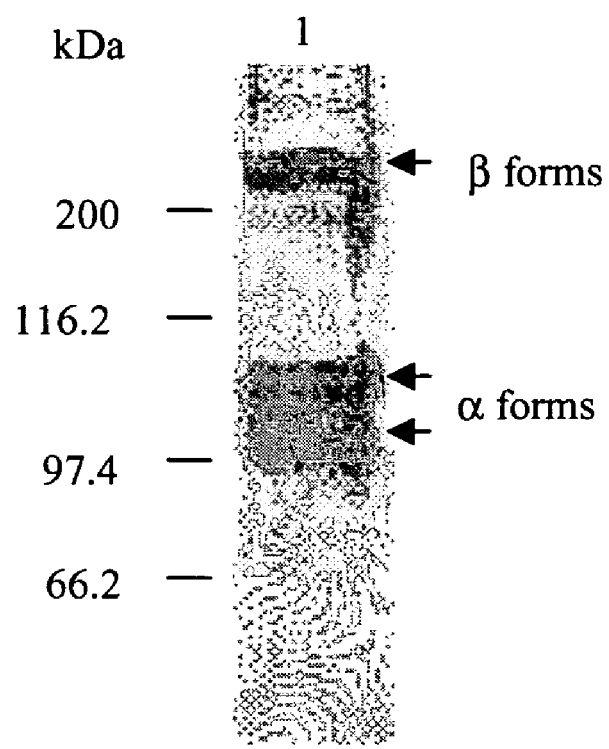
FIG. 2 is the result of polyacrylamide gel electrophoresis of extracted avian collagen using bacterial fermentation.

At this stage, the composition and purity of the collagen-containing solution prepared from avian tissues were analyzed by SDS-7.5% polyacrylamide gel electrophoresis, see FIG. 2 which shows the extracted α and β forms of the collagen and their respective weight. The α form of the collagen monomer weighs around 95-100 kDa. The β form weighs around 200 kDa. The extracted collagens are well-preserved α and β forms weighing respectively around 100 to 200 kDa. The result shows more collagen monomers were extracted.

After filtration, collagen-containing solution was stored frozen at −80° C. and then lyophilized to produce avian type I collagen powder. The powder was carefully weighted and the weight of the recovered avian type I collagen was estimated to be 30% of the total initial tissues used. This is almost ten times the result of the collagen preparation method described in U.S. Pat. No. 5,106,949 where the collagen yield is at greater than about 4% of the wet weight of the finely divided tendon. U.S. Pat. No. 5,436,135 describes an extraction process where 180 g of final product comprising collagen type IV was extracted from 35.7 kg of placenta tissue as the starting material.

Example 3

Production of Collagen from Porcine Tissues Using Bacterial Fermentation

The skin of freshly slaughtered pig was first washed with double distilled water and followed by a second washing process to reduce contamination. This washing process uses a combination of treatments with 0.2N NaOH and 0.01~0.2% hypochlorite aqueous solution. The incubation time of each treatment ranges from 15 min to 40 min. After incubation, the treated pig skin was cut into small pieces (about 0.5 cm long and 0.5 cm width) and thoroughly washed with two successive washings using a pyrogenic water and air-dried.

A strain of Gram (+) bacterium belonging to the genus *Bacillus* was used in a fermentation process to extract collagen from the porcine skins. The bacterial culture grew in 25 ml nutrient broth at 37° C. for 24 hours in a shaking incubator at 150 rpm. It was then proportionally scaled up to 100 ml and transferred to a fermenter and allowed to grow for 24 hours. The agitation and aeration rate were set at 450 rpm and 3 vvm, respectively.

Then, the fermenter was loaded with tissues ranging from 10% to 40% (w/v) for fermentation. The agitation was adjusted to 350 rpm during the fermentation that can continue for 18~48 hours. After fermentation, tissues were recovered and washed by two successive washings with apyrogenic water.

Figure 3:
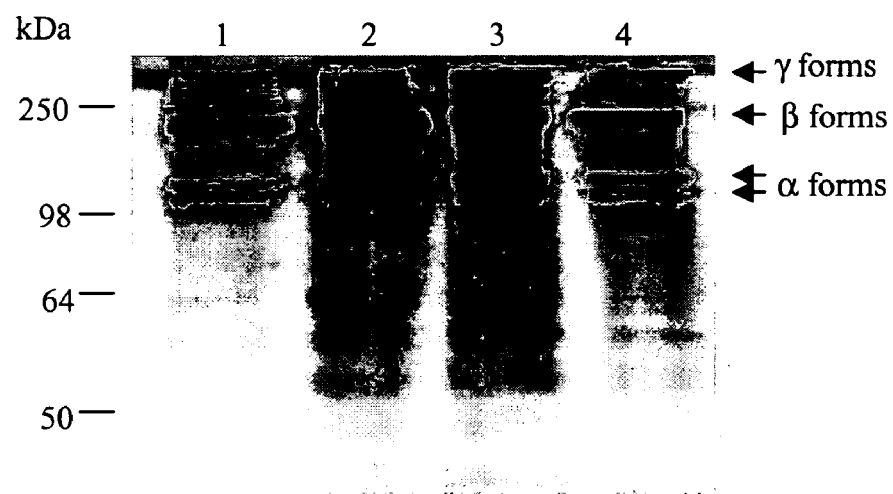
FIG. 3 is the result of polyacrylamide gel electrophoresis of extracted porcine collagen with commercial bovine collagen as the reference using bacterial fermentation.

Porcine collagen was extracted by dissolving the fermented tissues in an aqueous solution (3% w/v) containing 0.5M acetic acid (pH 3.0) and 0.4%~2% pepsin (w/v) with gentle stirring for not more than 48 hours, preferably 36 hours. After solubilization, the collagen-containing aqueous solution is filtered through active charcoal, followed by centrifugation at 5000×g for 50 minutes and the collagen content of the acid soluble fraction was analyzed by 10% SDS-PAGE, see FIG. 3 which shows α, β and γ forms of the extracted collagen and their respective molecular weight. Lane 1 contains 20 μg of porcine collagen; lane 2 contains 40 μg of porcine collagen; lane 3 contains 40 μg of commercial bovine; and lane 4 contains 20 μg of commercial bovine. Collagen monomers, α form and β form, were extracted weighing around 100 and 250 kDa respectively (Fluka pure bovine collagen was used as a reference).

Example 4

Production of Collagen from Aquatic Animal Tissues Using Bacterial Fermentation

About 10 g of shark skin was washed with water and air-dried for 30 minutes. A field isolate Gram (+) bacteria, belonging to the genus *Bacillus*, was cultured in nutrient medium at 37° C. for 24 hours with constant shaking at 150 rpm. 10 ul of fresh bacterial culture was inoculated into 125 ml hinton flask, containing 5 ml nutrient medium. It is then allowed to grow for 24 hours with constant shaking at 250 rpm. The content of the flask was proportionally scaled up to 100 ml and allowed to grow for another 24 hours. For the bacteria growth, the agitation and aeration rate were set at 450 rpm and 3 vvm, respectively.

The 10 gram of shark skin tissues was loaded into the flask containing the bacteria. The growth conditions remained unchanged. Fermentation proceeded for 24 hours at 37° C.

The fermented tissues were then recovered and mixed with an acidic solution (3% w/v) containing 0.5M acetic acid (pH 3.0) and 1% pepsin. They were incubated at 4° C. for 16 hours.

Figure 4:
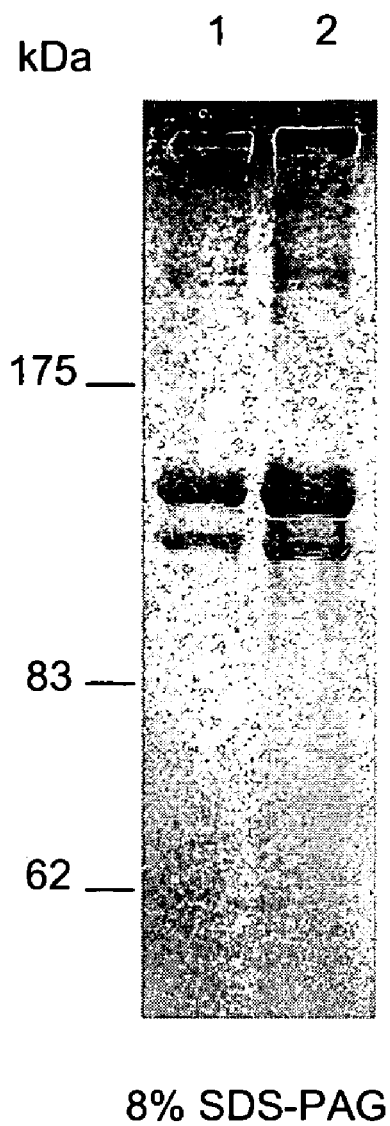
FIG. 4 is the result of polyacrylamide gel electrophoresis of extracted shark skin collagen using bacterial fermentation.

The insoluble tissues and debris were subsequently removed by centrifugation at 5000×g for 50 minutes. The supernatant was removed and mixed gently with 5M NaCl and incubated undisturbed at 4° C. overnight. The precipitated collagen was concentrated by centrifugation at 5000×g for 50 minutes. The resulting supernatant was discarded and the pellet recovered for 8% SDS-PAGE, see FIG. 4 Lanes 1 and 2 contain 10 μl and 20 μl of collagen respectively. FIG. 4 shows collagen extracted with molecular weight around 100 kDa, characteristic of collagen monomers.

Example 5

Production of Collagen from Avian Tissues Using Yeast Fermentation

Twenty (20) grams of chicken feet were washed with water and then air-dried. 10 ul of yeast was inoculated in 5 ml YPD medium at room temperature for 24 hours. 5 ml of yeast was inoculated into a 125 ml hinton flask containing 25 ml of nutrient medium. The inoculated yeast was allowed to grow for 24 hours at 120 rpm. The content of the flask was then proportionally scaled up to 100 ml.

The flask was then loaded with the 20 gram of chicken feet tissues and the bacteria. The growth conditions remained unchanged. Fermentation proceeded for 48 hours at 37° C.

The fermented tissues were then recovered and mixed with an acidic solution (5% w/v) containing 0.5M acetic acid (pH 3.0) and 1% pepsin. They were incubated at 4° C. for 16 hours.

Figure 5:
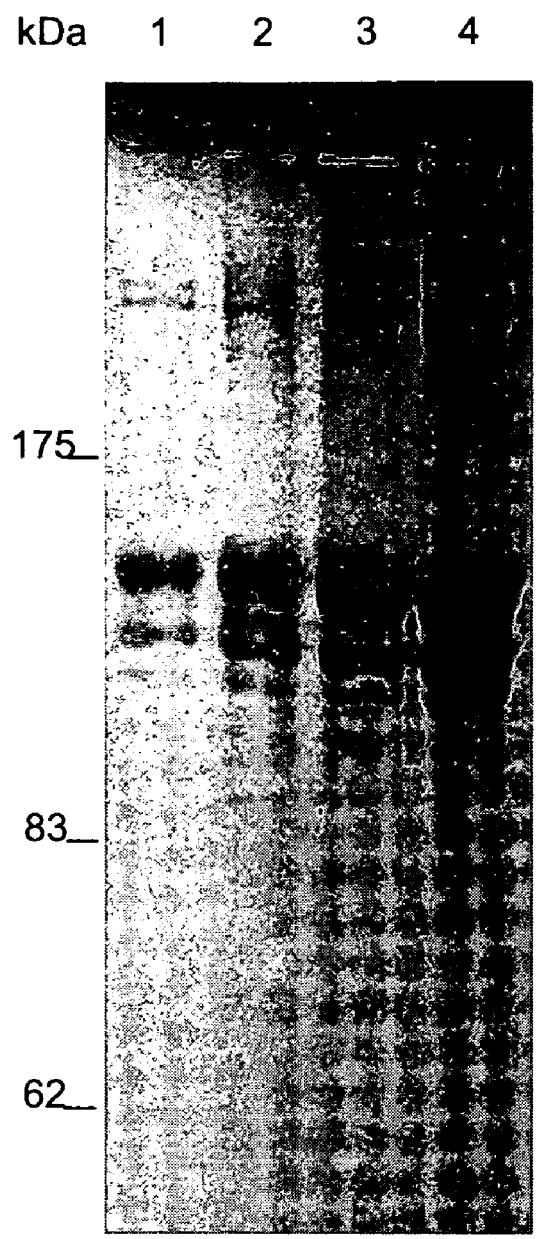
FIG. 5 is the result of polyacrylamide gel electrophoresis of extracted avian collagen using yeast fermentation.

The insoluble tissues and debris were subsequently removed by centrifugation at 5000×g for 50 minutes. The supernatant was removed and mixed gently with 5M NaCl and incubated undisturbed at 4° C. overnight. The precipitated collagen was concentrated by centrifugation at 5000×g for 50 minutes. The resulting supernatant was discarded and the pellet recovered for 8% SDS-PAGE, see FIG. 5. Lane 1 contains 5 μl of collagen; lane 2 contains 10 μl of collagen; lane 3 contains 20 μl of collagen; and lane 4 contains 40 μl of collagen. FIG. 5 shows collagen monomers extracted with molecular weight around 100 kDa.

Example 6

Type II Collagen Extraction from Cartilage

About 10 grams of cartilage from chicken rib were washed with tap water and then air-dried. A filed isolate Gram (+) bacterium, belonging to the genus *Bacillus*, was used in the fermentation process. The microorganism was cultured in nutrient medium at 37° C. for 24 hours with constant shaking at 150 rpm. Approximately 10 ul of fresh bacterial culture was inoculated into 125 ml hinton flask containing 5 ml nutrient medium, and allowed to grow for 24 hours with constant shaking at 250 rpm. The content of the flask was proportionally scaled up to 100 ml and allowed to grow for another 24 hours.

Prior to fermentation, the bacteria were transferred to a fermenter that contained nutrient medium. The bacteria was allowed to grow in the fermenter at 37° C. for 24 hours with the agitation and aeration rate set at 450 rpm and 3 vvm respectively. The cartilage was then loaded to the fermenter, and the growth conditions for the bacteria remained unchanged, except the agitation rate was adjusted to 350 rpm. Fermentation proceeded for 24 hours.

Figure 6:
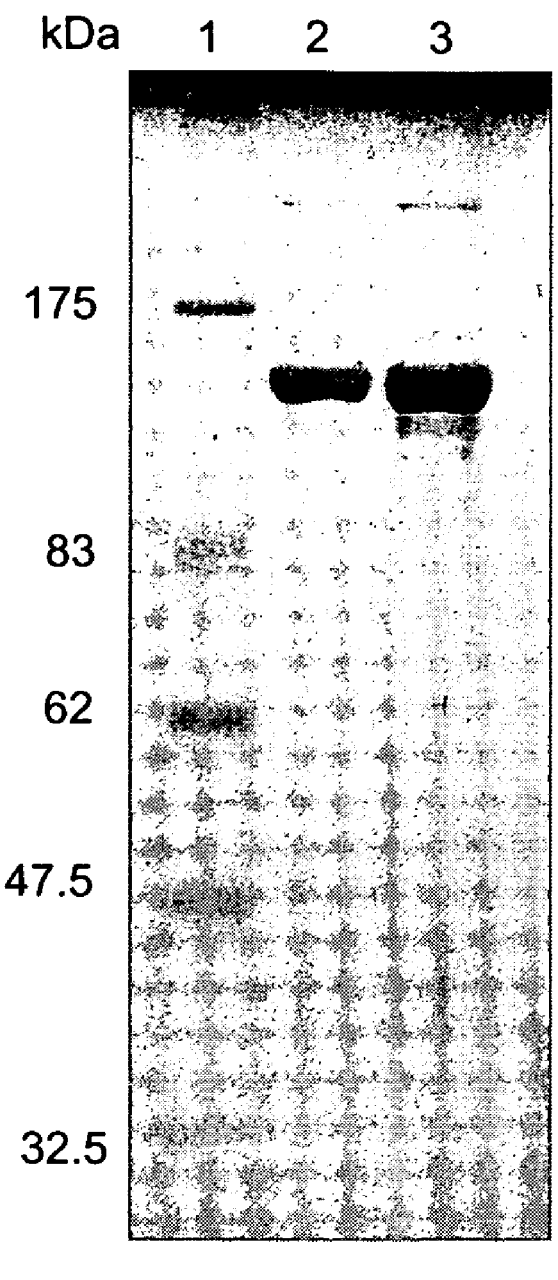
FIG. 6 is the result of polyacrylamide gel electrophoresis of collagen extracted from avian cartilage.

Upon completion of fermentation, the fermented cartilage tissues were separated from the culture broth and washed with double distilled water. The fermented tissues were then dissolved in 3% w/v acidic solution (0.5M at pH 3.0) containing 0.5M acetic acid (pH 3.0) and 1% pepsin and incubated at 4° for 48 hours. The insoluble tissues were then removed by centrifugation. The supernatant was then mixed gently with 5M NaCl and incubated at 4° C. to precipitate the collagen. The supernatant was subsequently discarded and pellets were recovered for 8% SDS-PAGE analysis, see FIG. 6. Lane 1 is the marker; lane 2 contains 5 μl of collagen; and lane 3 contains 10 μl of collagen. FIG. 6 shows clear single band of around 100 kDa, which is characteristic of type II collagen. This feature is distinct from type I collagen which usually shows two single bands around 100 kDa.

REFERENCES

The publications discussed in this application are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

What is claimed is:

1. A method of producing collagen monomers comprising:
    (a) contacting collagen-containing tissues with microorganisms wherein the collagen-containing tissues are obtained from one or more of mammals, aquatic animals, and avian animals, and wherein the microorganisms are bacteria or fungi;
    (b) allowing the microorganisms to ferment the collagen-containing tissues;
    (c) solubilizing the fermented tissues by the addition of an acidic solution and an enzyme preparation;
    (d) precipitating the collagen monomers; and
    (e) obtaining the precipitated collagen monomers,
wherein the precipitated collagen product comprises collagen monomers weighing at least 10% of the weight of the total collagen in said collagen product.

2. The method of claim 1, wherein the enzyme preparation comprises pepsin.

3. The method claim 1, wherein the precipitation is carried out by the addition of salt.

4. The method of claim 1, wherein the microorganisms are grown for more than 24, 48 or 72 hours before fermenting the collagen-containing tissues.

5. The method of claim 1, wherein fermentation is performed with agitation and aeration.

6. The method of claim 1, wherein the collagen product comprises collagen monomers weighing at least 50% of the weight of the total collagen in said collagen product.

7. The method of claim 1, wherein the microorganisms comprise generally regarded as safe (GRAS) microorganisms.

8. The method of claim 1, wherein the microorganisms are bacteria.

9. The method of claim 8, wherein the bacteria are Gram positive.

10. The method of claim 9, wherein the bacteria are of the genus *Bacillus*.

11. The method of claim 8, wherein the bacteria are Gram negative.

12. The method of claim 1, wherein the mammals are porcine or bovine.

13. The method of claim 1, wherein the aquatic animals are fish or shark.

14. The method of claim 1, wherein the avian animals are chickens.

15. The method of claim 1, wherein the collagen product comprises collagen monomers weighing at least 50% of the weight of the total collagen in said collagen product.

16. The method of claim 1, wherein the collagen product comprises collagen monomers weighing at least 80% of the weight of the total collagen in said collagen product.

17. The method of claim 1, wherein the microorganisms are fungi.

18. The method of claim 17, wherein the microorganisms are yeast.

19. A method of producing collagen monomers comprising:
  (a) contacting Gram (+) bacteria belonging to the genus *Bacillus* in a fermenter with collagen-containing tissues, wherein the collagen-containing tissues are obtained from one or more of mammalian, aquatic, or avian animal sources;
  (b) allowing the bacteria to ferment the collagen-containing tissues at about 10% w/v to about 40% w/v in the fermenter;
  (c) solubilizing the fermented tissues at about 1% w/v to about 50% w/v in an acidic solution of about 0.5M acetic acid (pH 3.0) with pepsin provided at about 0.2% w/v to about 5% w/v at low temperatures;
  (d) adding salt to the acidic solution sufficient to precipitate collagen and keeping it undisturbed overnight; and
  (e) obtaining the precipitated collagen monomers,
wherein the precipitated collagen product comprises collagen monomers weighing at least 10% of the weight of the total collagen in said collagen product.

20. The method of 19, wherein the collagen-containing tissues are fermented in the fermenter for about 18 hours to about 48 hours.

21. The method of claim 20, wherein the collagen-containing tissues are fermented at about 10% w/v in the fermenter for about 24 hours.

22. The method of claim 21, wherein the acidic solution is about 3% w/v of about 0.5M acetic acid (pH 3.0) with pepsin provided at about 1% w/v and further comprising stirring for about 48 hours when solubilizing the fermented tissues in the acidic solution.

23. The method of claim 22, wherein the avian source is chicken.

24. The method of claim 20, wherein the acidic solution is about 3% w/v of about 0.5M acetic acid (pH 3.0) with pepsin provided at about 0.4% w/v to about 2% w/v and further comprising stirring for not more than about 48 hours when solubilizing the fermented tissues in the acidic solution.

25. The method of claim 24, wherein the mammalian source is porcine or bovine.

26. The method of claim 19, wherein the low temperatures is at about 4° C.

* * * * *